Aug. 23, 1938. J. GAUJARD Plant Pat. 284
ROSE PLANT
Filed Sept. 18, 1937
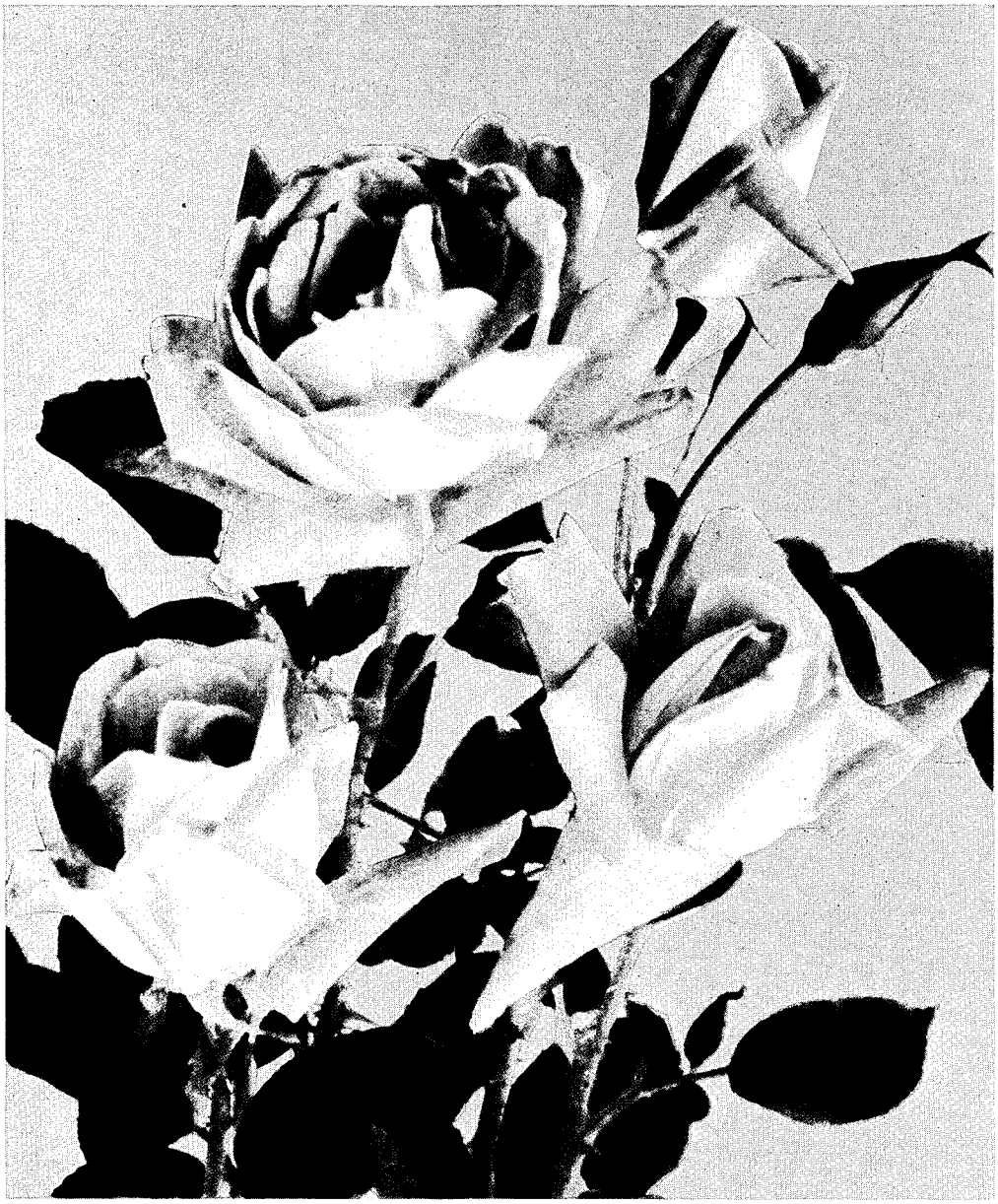
Inventor
Jean Gaujard
By Robb & Robb
attorneys Patented Aug. 23, 1938

UNITED STATES PATENT OFFICE

284

ROSE PLANT

Jean Gaujard, Feyzin, France, assignor to Jackson & Perkins Company, Newark, N. Y.

Application September 18, 1937, Serial No. 164,593

1 Claim. (Cl. 47—61)

The present invention is the result of a definite effort to produce a garden rose of the new class of hardy, decorative bedding roses with the high colored two tone effect of Austrian Copper.

In carrying out the objective, I crossed the Conrad F. Meyer (Rugosa hybrid) with an unnamed seedling of Austrian Copper many times without success because of the uncongeniality between the two strains, Rugosa and Austrian Copper. Finally one hip was produced on Conrad F. Meyer from which two seeds germinated, one of which grew into the new rose herein described.

This new variety has all the characteristics of Rugosa, is hardy and extremely spiny, but the bloom resembles a Hybrid Tea with the colors of Austrian Copper, gold-yellow outside and scarlet inside. The habit of growth is like an average Tea, spreading, and is especially adapted for mass planting for garden decoration.

Tests have been made over a number of years by budding on various understocks, and the variety has uniformly come true.

The following is a detail description of the new variety, reference therein to color according with the Gravereaux color standard, except where obviously the ordinary dictionary definition is intended:

Parentage:

*Seed parent.*—Conrad F. Meyer.

*Pollen parent.*—Unnamed seedling of Austrian Copper.

Classification:

*Botanic.*—Hybrid Rugosa—Foetida.

*Commercial.*—Hybrid Tea.

*Flower*

Blooming habit:

Observations were made for several years in the Jackson & Perkins fields and gardens.

Recurrent—Continuous.

Extremely prolific and steady blooming.

Bud:

*Size.*—Medium.

*Form.*—Long, pointed. Unaffected by wet or hot weather.

*Color.*—When sepals first divide—Nankin. When petals begin to unfurl—Nankin. When half blown:—Inside of petals—scarlet. Reverse of petals—Nankin.

*Sepals.*—Smooth edge, "hood" above bud. Curl back when bloom opens.

*Calyx.*—Shape—funnel. Size—broad. Aspect—smooth. Odor when rubbed—russet apple.

*Peduncle.*—Length—long. Aspect—rough. Color—medium green. Strength—stiff. heavy.

*Opening.*—Bud opens well. Is not affected by adverse conditions.

Bloom:

*Size.*—medium. Average size when fully expanded—3½ inches.

*Borne.*—Several together.

*Stems.*—Medium, strong.

*Form.*—Cupped, retains its form to the end.

*Petalage.*—Double. Number of petals under normal conditions—25.

*Color.*—Center of flower—scarlet. Outer petals—scarlet. Base of petals—gold. Inside of petals—scarlet. Reverse of petals—Nankin. General tonality from a distance—bicolor, red and yellow.

*Variegations.*—None.

*Discoloration.*—First and second days—none. Third day—both scarlet and Nankin pale considerably, the Nankin being almost white and the scarlet turning toward pink.

Petals:

*Texture.*—Thick. Is not affected by wet or hot weather.

*Appearance.*—Inside—shiny. Outside—satiny.

*Form.*—Round.

*Arrangement.*—Informal (with "rags" in center). Petaloids in center—few, small.

*Persistence.*—Drop off cleanly.

*Fragrance.*—Moderate. Nature—fruity (russet apple).

*Lasting quality on the plant and as cut flower.*—Very long.

Genital organs:

*Stamens, anthers.*—Large, many. Color—canary. Arrangement—regular around styles.

*Stamens, filaments (threads).*—Medium. Color—canary.

*Pollen.*—Lemon.

*Styles.*—Loosely separated, uneven length; medium length, heavy.

*Stigmas.*—Lemon.

*Ovaries.*—All enclosed in calyx.

Fruit:

Variety is sterile with its own pollen.

*Plant*

Form:

Bush.

Growth:

Vigorous, branching.

Foliage:

Generally five leaflets.

*Size.*—Medium.

*Quantity.*—Abundant.

*Color.*—New foliage—bronzy. Old foliage—upper side—dark green. Under side—lighter green.

*Shape.*—Oval pointed.

*Texture.*—Upper side—leathery. Under side—smooth. Ribs and veins—ordinary.

*Edge.*—Serrated.

*Serration.*—Single.

*Rachis.*—Color—green, reddish. Under side—prickles.

*Stipules.*—Medium, smooth.

*Disease resistance.*—Resistant.

Wood:

*New wood.*—Color—bronzy. Bark—rough.

*Old wood.*—Color—green, brown. Bark—smooth.

Thorns (divided into thorns, prickles and short needles):

*Thorns.*—Quantity—on main stalks from base—many. On laterals from stalk—many. Form—broad base, medium, straight. Color when young—red. Position—irregular.

*Prickles.*—Quantity—on main stalks—many. On laterals—many. Color—brown.

*Short needles.*—Quantity—on main stalks—many. On laterals—many.

I claim:

A new and distinct variety of rose plant, substantially as shown and described, resulting from the cross of the two strains Rugosa and Austrian Copper, having the characteristics of Rugosa, and the Hybrid Tea type of bloom of two tone color, adapted particularly for mass planting for garden decoration.

JEAN GAUJARD.